(12) United States Patent
Sontag et al.

(10) Patent No.: US 6,298,260 B1
(45) Date of Patent: *Oct. 2, 2001

(54) RESPIRATION RESPONSIVE GATING MEANS AND APPARATUS AND METHODS USING THE SAME

(75) Inventors: Marc R. Sontag, Cordova; Bentley H. Burnham, Germantown, both of TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/374,831

(22) Filed: Aug. 14, 1999

Related U.S. Application Data

(63) Continuation-in-part of application No. 09/129,812, filed on Aug. 6, 1998, now Pat. No. 6,076,005.
(60) Provisional application No. 06/075,990, filed on Feb. 25, 1998.

(51) Int. Cl.[7] ..................................................... A61B 5/055
(52) U.S. Cl. ........................ 600/413; 600/428; 600/437; 378/62; 378/65
(58) Field of Search .................................. 600/407, 411, 600/413, 425, 427, 428, 436, 437, 439, 473, 476; 607/100, 1, 2, 96, 98, 115, 154–156; 378/62–65; 250/370.08, 370.09, 370.1; 324/307, 309

(56) References Cited

U.S. PATENT DOCUMENTS

| | | |
|---|---|---|
| 3,524,058 | 8/1970 | Roberson et al. . |
| 3,871,360 | 3/1975 | Van Horn et al. . |
| 3,993,995 | 11/1976 | Kplan et al. . |
| 4,163,901 | 8/1979 | Azam et al. . |
| 4,387,722 | 6/1983 | Kearns . |
| 4,663,591 | 5/1987 | Pelc et al. . |
| 4,726,046 | 2/1988 | Nunan . |
| 5,067,494 | 11/1991 | Rienmueller et al. . |
| 5,419,327 | 5/1995 | Rohedder . |
| 5,485,833 | 1/1996 | Dietz . |
| 5,511,553 | 4/1996 | Segalowitz . |
| 6,076,005 | * 6/2000 | Sontag et al. ........................ 600/413 |

FOREIGN PATENT DOCUMENTS

| | | |
|---|---|---|
| 0093897 | 11/1983 | (EP) . |
| 0336620 | 10/1989 | (EP) . |
| 0377764 | 7/1990 | (EP) . |

OTHER PUBLICATIONS

Ahmad et al., Radiother Oncol 42:87–90;1997.
Balter et al., Int J Radiat Oncol Biol Phys 36:167–74;1996.
Bohning et al., Magn Reson Med 16:303–16;1990.
Butts et al., Magn Reson Med 33:1–7;1995.
Davies et al., Br J Radiol 67:1096–102;1994.
Inada et al., Nippon Igaku Hoshasen Gakkai Zasshi 52:1161–7;1992.

(List continued on next page.)

*Primary Examiner*—Brian L. Casler
(74) *Attorney, Agent, or Firm*—Klauber & Jackson

(57) ABSTRACT

A method and system for gating therapeutic or diagnostic energy to a tissue volume of a medical patient during a selected portion of the patient's respiratory cycle, to thereby diminish inaccuracies in the assumed spatial position of the tissue volume arising from displacements induced by the patient's respiration. The gases flowing to and from the patient's lungs are monitored to provide quasi-continuous measurements as a function of time, for any selected subset of (a) flow rate, (b) pressure, (c) patient lung volume and (d) carbon dioxide concentration. The measurements are utilized to trigger the time period during which the energy is gated on, at the beginning of the selected portion of the respiration cycle; and the time period during which the energy is gated on, is terminated at the end of the selected portion of the respiration cycle.

36 Claims, 5 Drawing Sheets

OTHER PUBLICATIONS

Korin et al., Magn Reson Med 23:172–8;1992.
Kubo et al.,Phys Med Biol, 41:83–91;1996.
Landberg et al., International Commission on Radiation Units and Measurements, 50, 1993.
.Li et al., Radiology 201:857–63;1996.
Moerland et al., Radiother Oncol 30:150–4;1994.
Mori et al., 1994, AJR Am J Roentgenol, 162:1057–62.
Ohara et al., Int J. Radiat Oncol Biol Phys, 17:853–7; 1989.
Ohara et al., Nippon Igaku Hoshasen Gakkai Zasshi 47:488–96;1987.
Okumura et al., Proceedings of the XIth International Conference on the Use of Computers in Radiation Therapy :358–9;1994.
Ritchie et al., Radiology, 190:847–52; 1994.
Sade et al., J. Endourol 8:329–30;1994.
Schwartz et al., Radiother Oncol 32:84–6;1994.
Sontag et al., Medical Physics 23:1082;1996.
Suramo et al., Acta Radiol [Diagn] (Stockh) 25:129–31;1984.
Ten Haken et al., Int J Radiat Oncol Biol Phys 38:613–7;1997.
Voss, A. C. et al., Strahlentherapie 150:551–6;1975.
Wang, Y.; Riederer, S.J.; Ehman, R. L. Respiratory motion of the heart: kinematics and the implications for the spatial resolution in coronary imaging. Magn Reson Med 33:713–9;1995.
Wang,et al., Radiology 198:55–60;1996.
Wang et al., Magn Reson Med 36:579–87;1996.
Weiss et al., J Nucl Med 13:758–9;1972.

* cited by examiner

RESPIRATION RESPONSIVE GATING MEANS AND APPARATUS AND METHODS USING THE SAME

CROSS REFERENCE TO RELATED APPLICATION

This application is a continuation-in-part of application Ser. No. 09/129,812, filed Aug. 6, 1998 now U.S. Pat. No. 6,076,005, which, in turn, claims priority from Provisional Patent Application Ser. No. 60/075,990. The disclosures of both applications are incorporated herein by reference in their entireties, and applicants claim the benefits of 35 USC §119(e) and §120, where applicable.

FIELD OF INVENTION

This invention relates generally to apparatus and methods for use in therapeutic treatment and in diagnosis of medical patients. More specifically the invention relates to apparatus and methods which provide incident therapeutic or diagnostic energy to a medical patient during a selected portion of the patient's respiratory cycle, thereby diminishing inaccuracies in the assumed spatial location of the portion of the patient being treated or diagnosed which arise from the patient's respiration. The invention is applicable to diagnostic or therapeutic treatment with electromagnetic, sonic or other incident energy, including therapeutic treatment and diagnostic procedures based on x-rays, gamma rays, or visible or near visible radiation; energy fields which are incident to MRI; and/or energy rendered incident on the patient by detectable charged or uncharged particle beams.

BACKGROUND OF INVENTION

Although the invention is broadly applicable as above indicated, the problem to which it is addressed is especially well illustrated by considering the field of radiation therapy. A principal goal of such therapy is to deliver a radiation dose appropriate to achieve the purpose of treatment (e.(g. tumor eradication, palliation), while simultaneously minimizing dosage to surrounding normal (healthy) tissues, reducing the likelihood of clinically significant damage to these tissues. These objectives may be appreciated by referring to the schematic depiction of FIG. 1, which illustrates the ICRU definitions for appropriate target volumes for a patient undergoing radiation therapy. (See landberg, T. Chavaudra, J.; Dobbs, J.; Hanks, G.; Johansson, K.; Moller, I.; Purdy, J.; "Prescribing, Recording, and Reporting Photon Beam Therapy". International Commission on Radiation Units and Measurements, 50, 1993. The Gross Tumor Volume (GTV) is the gross palpable or visible/demonstrable extent and location of malignant growth. The Clinical Target Volume (CTV) is a tissue volume that contains a demonstrable GTV and/or subclinical microscopic malignant disease, which has to be eliminated. This volume thus has to be treated adequately in order to achieve the aim of therapy, cure or palliation. The Planning Target Volume (PTV) is a geometrical concept, and it is defined to select appropriate beam sizes and beam arrangements, taking into consideration the net effect of all the possible geometric variations, in order to ensure that the prescribed dose is actually absorbed in the CTV. The Treated Volume is the volume enclosed by an isodose surface, selected and specified by the radiation oncologist as being appropriate to achieve the purpose of treatment (e.g. tumor eradication, palliation). The gross target volume (GTV) and clinical target volume (CTV) thus contain tissues to be treated, while the planning target volume (PrV) places a margin around the CTV to account for patient movement and uncertainties in treatment set up.

In the last several years, conformal therapy techniques are being used with increasing frequency. These techniques combine good patient immobilization to minimize the PTV margin around the CTV coupled with the use of multiple, non coplanar beams to reduce treated volume margin beyond the PTV. The ultimate goal of conformal therapy is to deliver a treatment in which the CTV, PTV and treated volumes are identical. The use of intensity modulated radiotherapy (IMRT) and multiple, non coplanar beams has substantially improved the conformation of the treated volume to the PTV.

In the thorax and abdomen, the PTV margin beyond the CTV remains relatively large. A large contributory factor is the organ motion due to respiration. Motion of the heart, kidney, liver, pancreas, and spleen may be several centimeters, requiring a large PTV. In diagnostic imaging, organ motion has been recognized as a significant cause of image blurring. Several techniques may be used to reduce respiratory organ motion. Retrospective or prospective image correction techniques such as navigator echo imaging work well for MRI, but are not applicable to radiation therapy. Breath holding has been used with success for spiral CT scanner image acquisition but is not practical for radiation therapy, because the beam on time is typically too long for most patients to hold their breath. In lithotripsy, respiratory induced kidney motion inhibits accurate localization.

In radiation therapy, the potential reduction in the PTV margin, accomplished by minimizing the effects of organ motion due to respiration, may be as great as the reduction in the treated volume margin gained by using conformal therapy techniques. Yet, methods to reduce organ motion in radiation therapy have been limited and typically have employed impedance plethysmography or pneumotachometry, measuring changes in chest or abdomen position or pressure, usually by means of a sensor such as a belt attached to the patient. These devices may have calibration problems caused by variation of the tightness of the belt between treatments or slippage that occurs during treatment. If the device is in the beam, radiation damage to the device or loss of skin sparing may occur. In radiation therapy, the challenge is not simply to freeze respiratory motion for a single session, as is the case in diagnostic imaging, but to do so reproducing the diaphragm position between consecutive respiratory cycles, radiation beams and treatment days. The procedure employed must ensure reproducibility of organ position not only during treatment but for diagnostic image acquisition used in treatment planning as well.

SUMMARY OF INVENTION

Now in accordance with one aspect of the present invention, a method is provided for gating therapeutic or diagnostic energy to a tissue volume of a medical patient during a selected portion of the patient's respiratory cycle, to thereby diminish inaccuracies in the assumed spatial position of the tissue volume arising from displacements induced by the patient's respiration. Pursuant to the method the gases flowing to and from the patient's lungs are monitored to provide quasi-continuous measurements as a function of time, of at least two of (a) flow rate, (b) pressure, (c) patient lung volume and (d) carbon dioxide concentration. Preferably measurements of all four of these parameters are provided. These measurements are used to trigger the time period during which the said energy is gated at the beginning of the selected portion of the respiration cycle; and optionally to terminate the time period during which the said energy is gated, at the end of the selected portion of the respiration cycle. Alternatively the energy gating period can be terminated independently of measurements (a) through (d).

The selected portion of the respiration cycle may start at substantially full exhalation and can include a respiration hold introduced in the cycle by the patient at substantially full exhalation. In such circumstances and assuming that all four of the mentioned parameters are measured, the energy is gated on when at the same time (1) the gas flow rate and pressure are below predetermined thresholds; (2) the lung volume is below a predetermined threshold; and (3) the carbon dioxide level is above a predetermined threshold. The predetermined thresholds for the four individual channels are set as follows: The pressure threshold is set as a user defined fraction of the previous pressure peak value (the last maximum before the signal crosses zero). When the pressure falls below the calculated level, the gate for that particular signal is opened ("ON"). When the pressure rises above the calculated level, the gate for that particular signal is closed ("OFF"). Flow is handled identically. The threshold for $CO_2$ is chosen graphically utilizing the display of a computer forming part of the system that will he further described below. In training mode, a trace of the $CO_2$ is represented on the computer screen and a moving bar is dragged up and down indicating the desired predetermined level for $CO_2$ to gate on. When $CO_2$ exceeds this level the gate for that signal is opened. The gate is closed when $CO_2$ falls below 90% of the predetermined level OR when the first derivative of $CO_2$ concentration as a function of time is less than a fixed negative value. Because a heartbeat during full exhalation may cause the lungs to draw in a small bit of air and expel it again by the time the heartbeat ends ("cardiogenic oscillations"), causing a brief drop then restoration of the $CO_2$ level, a second check of $CO_2$ level is required. If after 150 msec the $CO_2$ level remains below the predeterminied level, the gate signal is closed. If within 150 msec the $CO_2$ level rises again above the threshold, the gate signal remains open.

The threshold for volume is also chosen graphically. Due to the functioning of the respiratory monitor, the absolute value of the volume is not always well known, however the peak to peak difference between crest and trough is very reproducible. Therefore in training mode, two moving bars are used to set upper and lower bounds on the volume trace. The absolute difference between the two bars is used as the threshold. When the volume falls from its previous maximum value by an amount greater than the threshold, the gate is opened. When the difference is again less, the gate is closed.

All four respiratory parameters or any subset thereof of at least two such parameters may be used. Although in principle even a single parameter could be used, the present method by using at least a pair of such parameters, vastly increases the reliability of the measurements over the case where a single parameter is depended upon. Unused parameters are bypassed by setting the associated gates permanently open. For example, for a lightly breathing patient, only CO2 and lung volume might be monitored, permanently opening the air low and pressure gates. A triggering signal is sent only when all four gates are open. Closing of any one of the gates results in termination of the trigger signal. Termination may be delayed by a user defined time period. Any or all of the gates may be opened permanently by the user.

The method of the invention can also be practiced where the selected portion of the respiration cycle is initiated at substantially full inhalation. A hold can be introduced in the respiration cycle by the patient at said substantially full inhalation. The predetermined levels ("thresholds") for the four individual channels are set here as follows:

The pressure threshold is set as a user defined fraction of the previous pressure peak value (the last maximum before the signal crosses zero). When the pressure falls below the calculated level, the gate for that particular signal is opened ("ON"). When the pressure rises above the calculated level, the gate for that particular signal is closed ("OFF"). Flow is handled identically. The threshold for $CO_2$ is chosen graphically. In training mode, a trace of the $CO_2$ is represented on the screen and a moving bar is dragged up and down indicating the desired predetermined level for $CO_2$ to gate on. When $CO_2$ falls below this level, the gate is opened. The gate is closed when $CO_2$ rises above the predetermined level OR when the first derivative of $CO_2$ concentration as a function of time is greater than a fixed positive value. The threshold for volume is also chosen graphically. In training mode two moving bars are used to set upper and lower bounds on the volume trace. The absolute difference between the two bars is used as the threshold. When the volume is greater than its previous minimum value by an amount greater than the threshold, the gate is opened. When the difference is again less, the gate is closed. A triggering signal is sent only when all tour gates are open. Closing of any one of the gates results in termination of the trigger signal. Termination may be delayed by a user defined time period. Any or all of the gates may be opened permanently by the user.

In the method of the invention the selected portion of the respiratory cycle can also be centered about full exhalation.

The measurements carried out in the invention may be utilized to control a gating signal which activates a source of the energy. The term "activates" is used in the broad sense of enabling the energy from the source to impinge upon the patient. Thus the term is meant to encompass not only a situation where the source is dormant, e.g. an x-ray source requiring an electrical input as a prerequisite to production of x-rays; but also a case where the source is one which continuously generates energy—e.g. a radioactive source, and where "activation" of the source means opening of a shutter or other occluding mechanism.

In accordance with a further aspect of the invention, a system is disclosed for gating therapeutic or diagnostic energy to a tissue volume of a medical patient during a selected portion of the patient's respiratory cycle, to thereby diminish inaccuracies in the assumed spatial position of the tissue volume arising from displacements induced by the patient's respiration. The system includes a controllable source of energy for gating the energy to the patient tissue volume in response to an ON/OFF control signal. Means are provided for monitoring the gases flowing to and from the patient's lungs and providing quasi-continuous measurements as a function of time for any selected subset of (a) flow rate, (b) pressure. (c) patient lung volume and (d) carbon dioxide concentration. Preferably such means monitor and measure all four of the said parameters. Means are provided for utilizing said measurements to trigger the source control signal to ON at the beginning of the selected portion of the respiration cycle, and for triggering the control signal to OFF it the end of the selected portion of the respiration cycle.

Pursuant to the invention the energy source can be one that generates x-rays, other forms of electromagnetic energy (including e.g. laser sources), a generator of sonic energy, a generator of an activating field for MRI, a particle beam source, etc. The means for triggering the control signal to OFF may effect said triggering in response to said measurements; or the means for triggering the control signal to OFF may effect the triggering independent of said measurements such as by triggering the control signal to OFF as a function of elapsed time from the triggering of said control signal to ON. The selected portion of the patient's respiratory cycle may typically start at full inhalation, at full exhalation, or centered about full exhalation, or other portions of the respiratory cycle may be selected.

DESCRIPTION OF PREFERRED EMBODIMENT

Figure 1:
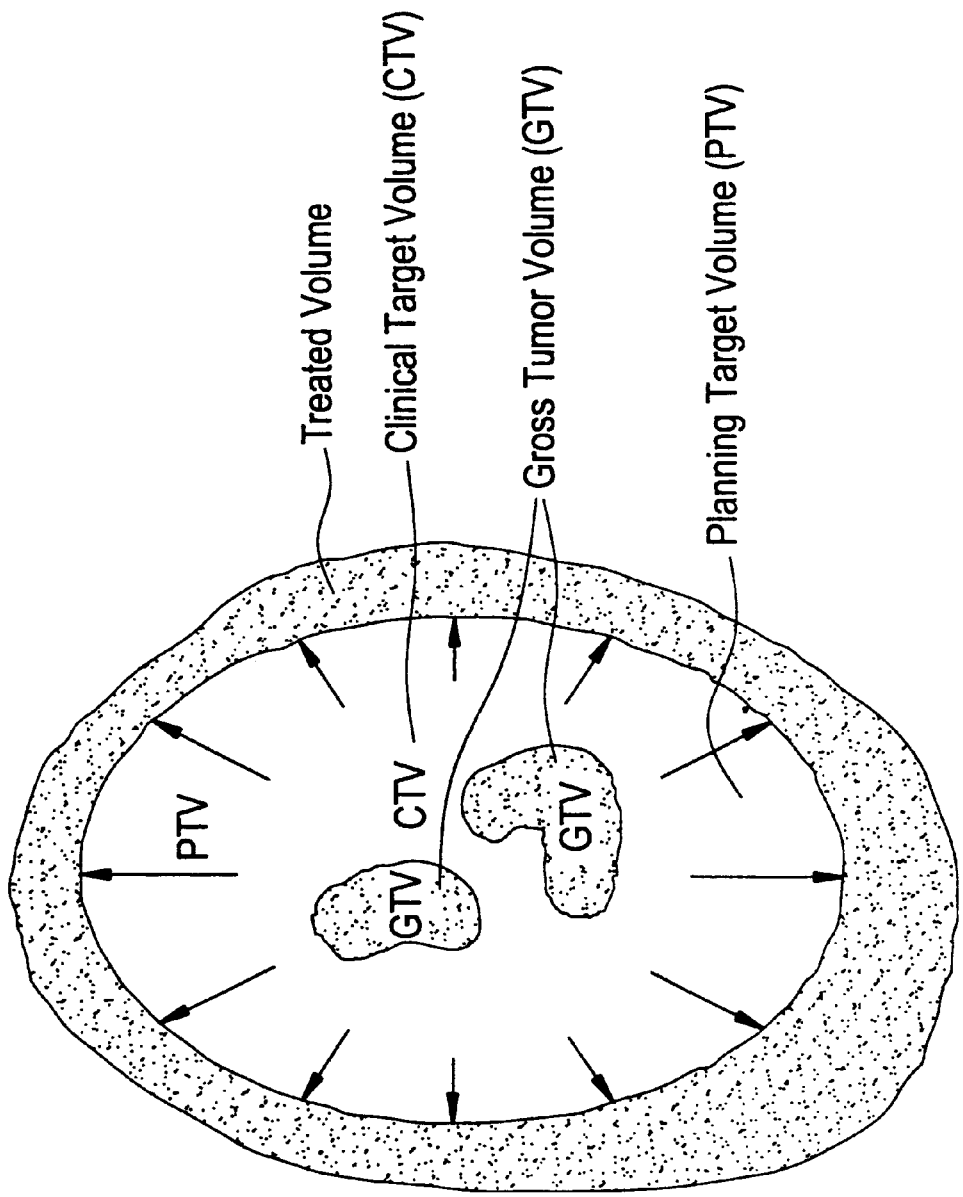
FIG. 1 is a schematic depiction illustrating the ICRU definitions for a patient undergoing radiation therapy.
Figure 2:
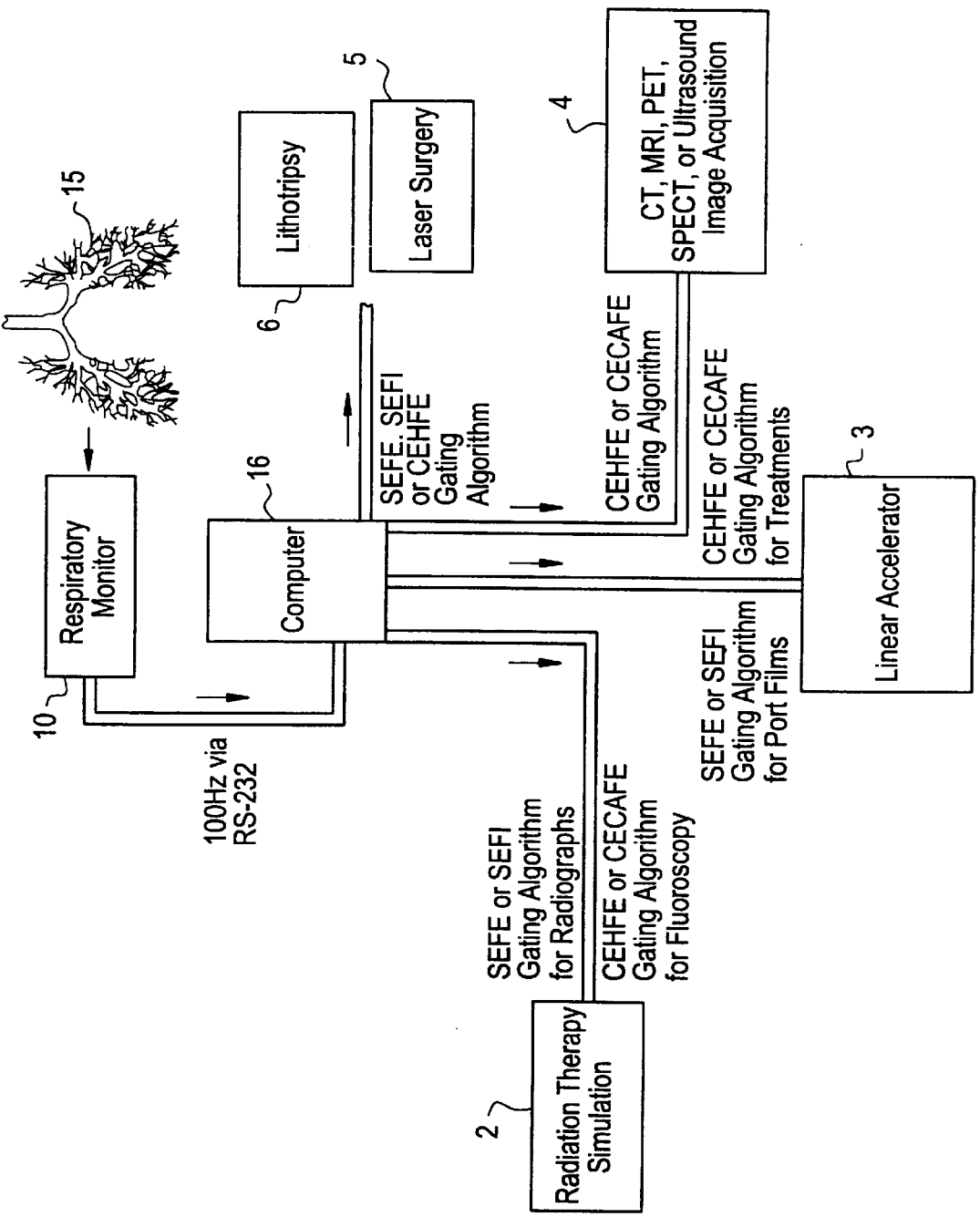
FIG. 2 is a schematic depiction of the respiratory gating system consisting of a respiratory monitor, control system and gated medical devices.

In FIG. 2, the generalized arrangement of a system operating in accordance with the invention is schematically illustrated. The respiratory input and output from the lungs of a patient 15 to be treated is connected to a respiratory monitor 10 which provides the data outputs of interest to a computer 16. Various medical devices can then be triggered ON and OFF in accordance with the needs of the examination or treatment, such as radiation therapy apparatus 2, linear accelerator 3, CT, MRI, PET, SPECT, or ultrasound image acquisition apparatus 4; laser surgery apparatus 5, or lithotripsy apparatus 6. Depending on the specific requirements of the examination or treatment, an appropriate algorithm is utilized, as illustrated, where the abbreviations shown respectively mean: SEFE=single exposure full exhalation, SEFI=single exposure full inhalation: CEHFE= continuous exposure hold at full exhalation; and CECAFE= continuous exposure centered about full exhalation.

Figure 3:
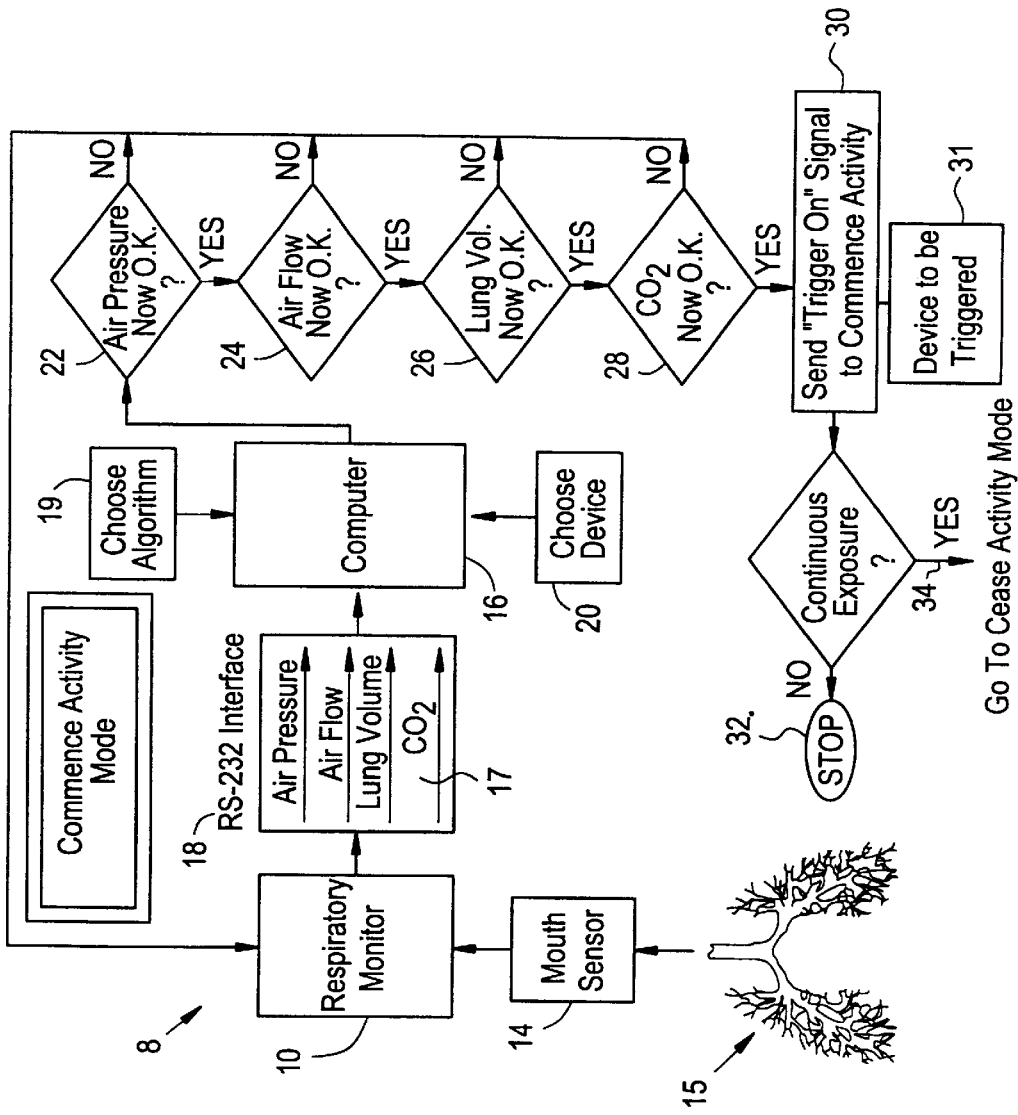
FIG. 3 is a schematic flow diagram, illustrating the initiation of energy gating in accordance with the principles of the invention.
Figure 4:
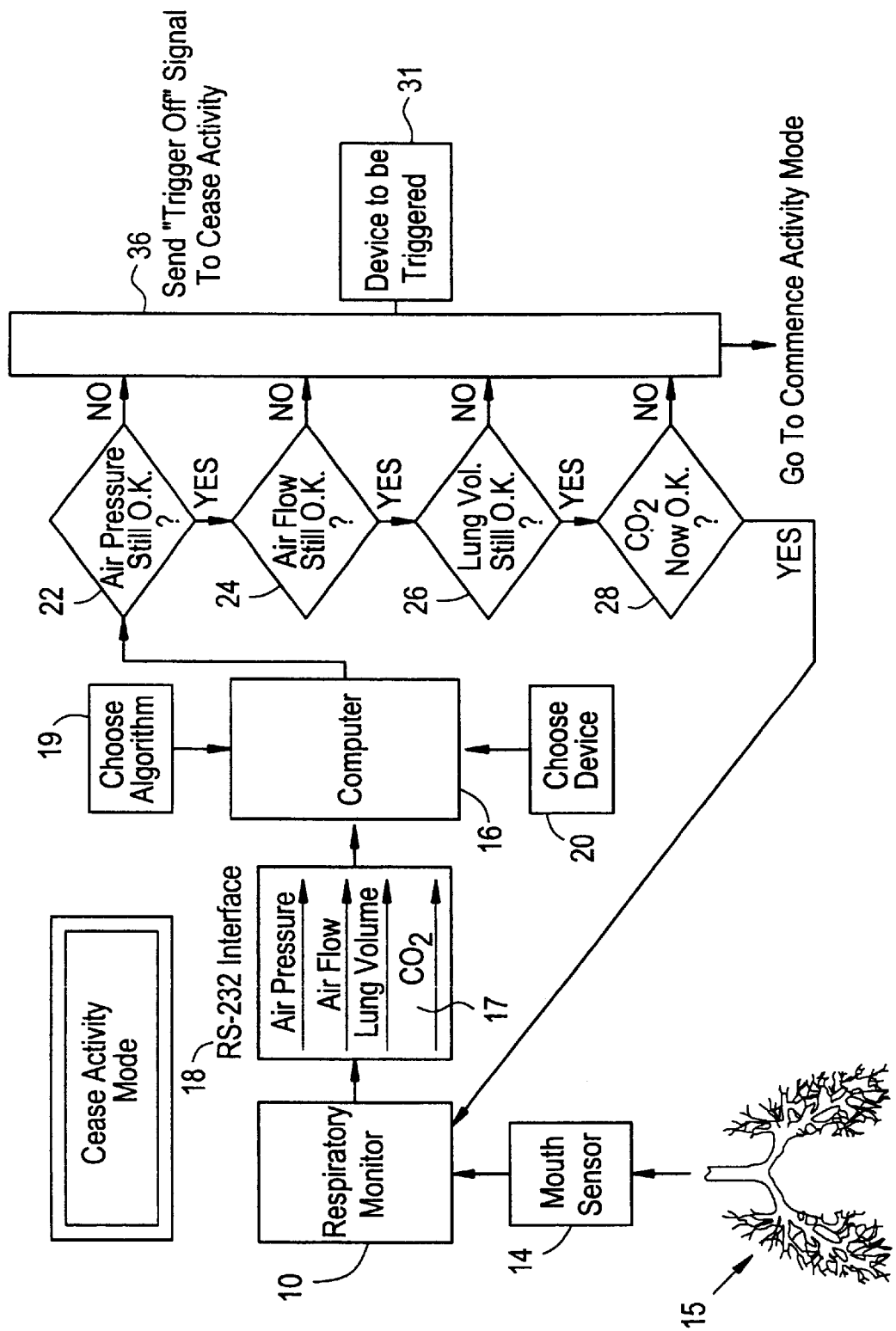
FIG. 4 is a schematic flow diagram, illustrating the termination of energy gating in accordance with the invention.

Referring to FIG. 3 and 4, a system 8 is schematically depicted, operating in accordance with the principles of the invention. The COMMENCE ACTIVITY mode is shown in FIG. 2, and the CEASE ACTIVITY mode in FIG. 3. A respiratory monitor 10 (available e.g. from Novametrix, Wallingford, Conn.) is used to characterize the respiratory mechanics for a patient 15. Monitor 10 employs a capnograph, which measures $CO_2$ using, an infrared sensor and a differential pressure pneumotachometer, which measures airway pressure and calculates both airway flow and lung volume. A sensor 14 is placed in the patient's mouth and the patient 15 is instructed to breathe normally through the mouth. If necessary, the nose can be clamped. Acquiring, readings through the mouth avoids the calibration and loss of skin sparing problems associated with devices such as belts placed around the abdomen or thorax. Readings for any or all of the tour respiratory parameters 17 ($CO_2$, flow, pressure and volume) are obtained 100 times per second (or on other quasi-continuous basis) and transmitted to computer 16 via an interface 18 such as an RS-232 serial port, to enable real time analysis. Parameter thresholds (as previously discussed) are adjusted based on a set of training data obtained immediately prior to image acquisition or treatment. At the computer 16 all algorithm is chosen (at 19) which is appropriate to the therapy or diagnosis which patient 15 is undergoing. The computer 16 is also provided an input 20 indicative of the diagnostic or therapeutic apparatus being used. Considering the case where all four parameters are monitored and used, as seen at data flow boxes 22, 24, 26 and 28, when appropriate values are present for each of the gas flow, pressure, lung volume and $CO_2$ concentration, a TRIGGER ON signal is provided at 30. This actuates the energy source or otherwise permits energy from an already active source to be rendered incident upon patient 10 from the device 31, which may be one of the devices shown in FIG. 2. In instances where the source remains active for only a brief specified period after triggering, cessation of the energy incidence will automatically occur alter the specified pre-set time, as at 32. Where the source actuated is a continuous one, as at 34, the incidence energy upon the patient will continue until a TRIGGER OFF signal is generated, as at 36 in FIG. 4. The manner in which the TRIGGER OFF signal is generated is determined in accordance with the algorithm which is operable. The components of the system 8 are identified in the CEASE ACTIVITY mode showing of FIG. 4 with reference numerals corresponding to those used in FIG. 3.

In previous work of the present inventors, it was shown that the optimal time either to acquire images or to activate the beam of a device such as a linear accelerator is at the point of maximum exhalation. At this point in the respiratory cycle, the diaphragm position is most reproducible and the diaphragm velocity is at a minimum. Acquisition of a single x-ray image such as a radiograph on a radiation therapy simulator, is therefore suitably obtained using a "single exposure, full exhalation" (SEFE) algorithm. At the end of exhalation, air flow and pressure approach zero, lung volume is at a minimum, and $CO_2$ level is at a maximum. At the start of inhalation, the $CO_2$ level drops sharply (i.e. $\partial CO_2$ is negative), while the other parameters change more slowly from their end points. The large negative $\partial CO_2$ value is used to trigger image acquisition. Ensuring that the lung volume is below a preset value and the $CO_2$ level is above a preset value ensures that triggering doesnt occur at the wrong point in the respiratory cycle such as might occur when a patient inhales after having not fully exhaled. Triggering is allowed only when the separate and redundant analysis of all four respiratory parameters indicate it is appropriate. This minimizes false positives (exposing at an incorrect time) with only a small increase in false negatives (i.e. not exposing when it is acceptable). Each of the parameter thresholds is set interactively before image acquisition by obtaining a set of "training data" while the patient breaths normally. Triggering on a therapy simulator (Elekta, Atlanta, Ga.) is accomplished by sending the gating signal to a relay which closes the circuit controlled by the simulator foot pedal. This is the functional equivalent of depressing the foot pedal to produce an x-ray exposure.

It is often desirable to document the full range of organ motion. This is important, for example, when designing blocks for those cases in which gated linear accelerator treatments are not being used. This requires a second exposure at the point of full inhalation in addition to the one obtained at full exhalation. At full inhalation, air flow and pressure again approach zero, but $CO_2$, $\partial CO_2$ and lung volume values are reversed from full exhalation. Thus, with the "single exposure, full inhalation" (SEFI), triggering occurs when $\partial CO_2$ becomes sharply positive. The point of full inhalation is not as reproducible as full exhalation, but careful setting of the $CO_2$ and lung volume limits ensure exposure at the proper point. A doubly exposed radiograph documenting the two extreme diaphragm positions (full exhalation and full inhalation) can be obtained by using a double exposure algorithm which is a combination of the two single exposure algorithms described above (SEFE+SEFI).

In instances where the patient is able to effectively hold the breath at full inhalation or at full exhalation, an SEHFI or SEHFE algorithm may be useful. The parameters appropriate to actuate a TRIGGER ON and a TRIGGER OFF for these algorithms are shown in Tables 1 and 2.

TABLE 1

SEHFI Algorithm

| Respiratory Parameter | Trigger On Signal | Trigger Off Signal |
|---|---|---|
| Air Flow | Flow < fraction of immediately previous peak value. User selectable, typical value = 10% | Controlled by device being gated. |
| Air Pressure | Pressure < fraction of immediately previous peak value. User selectable, typical value = 10% | Controlled by device being gated. |
| Lung Volume | Current vol − Last Min Vol > Threshold. Threshold value set graphically, typically avg. diff between adjacent max and min lung volumes. | Controlled by device being gated. |
| $CO_2$ | $CO_2$ near 0 | Controlled by device being gated. |
| $\partial CO_2$ | Not Used | Controlled by device being gated. |
| Time | N/A | N/A |

TABLE 2

SEHFE Algorithm

| Respiratory Parameter | Trigger On Signal | Trigger Off Signal |
|---|---|---|
| Air Flow | Flow < fraction of immediately previous peak value. User selectable, typical value = 10% | Controlled by Device being Gated |
| Air Pressure | Pressure < fraction of immediately previous peak value. User selectable, typical value = 10% | Controlled by Device being Gated |
| Lung Volume | Last Max Vol − Current vol > Threshold. Threshold value set graphically, typically avg. diff between adjacent max and min lung volumes. | Controlled by Device being Gated |
| $CO_2$ | $CO_2$ > Threshold. User graphically selectable, typical value = 90% of maximum value. | Controlled by Device being Gated |
| $\partial CO_2$ | Not Used | Controlled by Device being Gated |
| Time | N/A | N/A |

The treatment simulator has a digital spot imager (DSI) that allows one to obtain digital images from the image intensifier at a rate of up to 8 images per second. Memory and heat restrictions usually limit this to 4 images per second. Images are obtained for several respiratory cycles (15–30 seconds) during normal respiration to document organ motion. Gating is accomplished with the floor pedal circuit in the same manner as for the single x-ray exposures.

Figure 5:
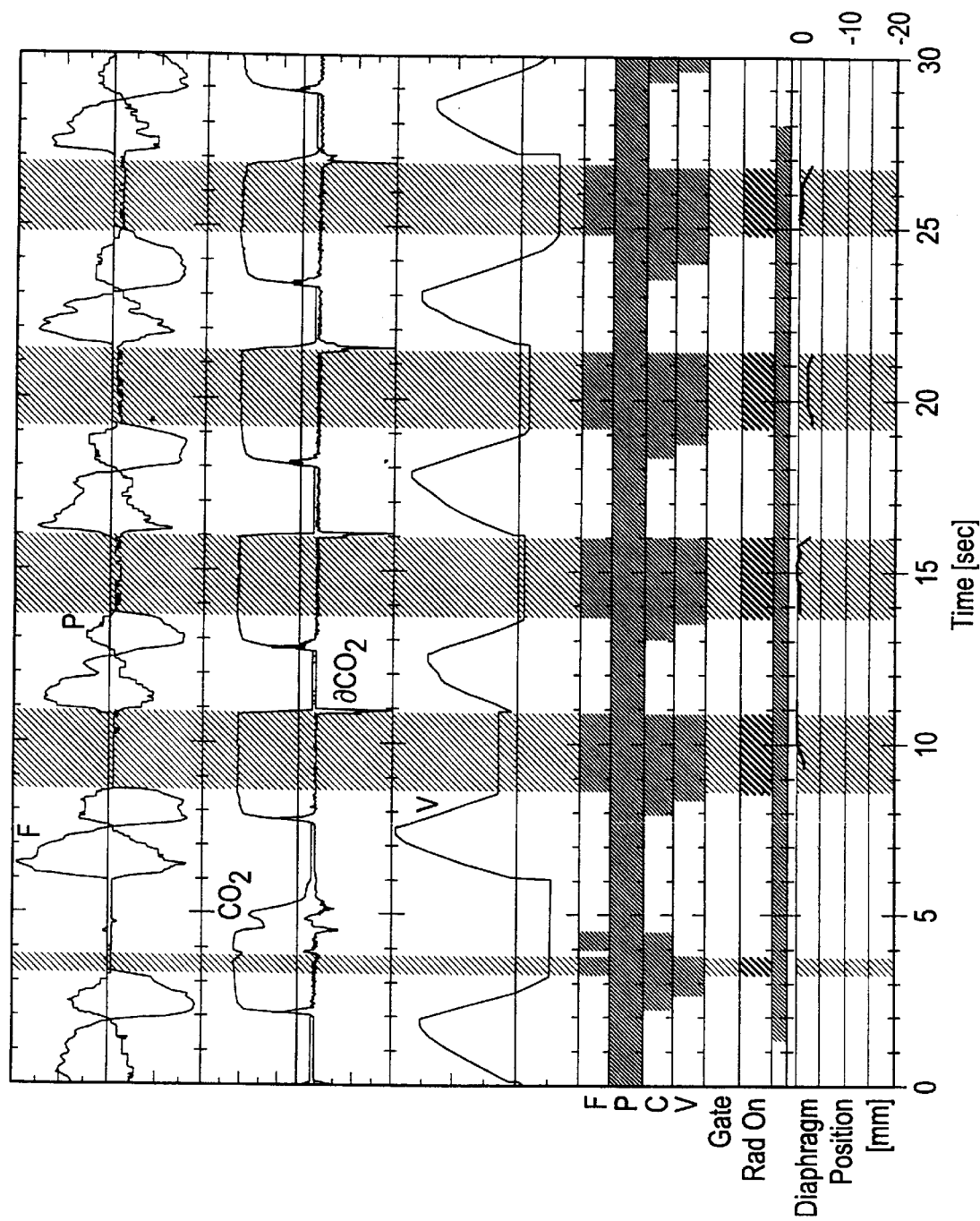
FIG. 5 is a graph depicting measurements taken during monitoring of gas flow to and from a patient who is being treated pursuant to the invention and illustrates how the measurements may be used in applying an algorithm of interest.

A "continuous exposure, hold at full exhalation" (CEHFE) algorithm is used to obtain images continuously with the diaphragm in a fixed, reproducible position. Patients are instructed to hold their breath for short periods of time, typically 2–3 seconds, after exhalation. Image acquisition commences when respiratory parameters are similar to those used by the SEFE algorithm, except for $\partial CO_2$ which is now equal to zero. (All references to derivatives herein, such as that to $\partial CO_2$, refer to the time rate of change of the function specified.) At the instant the patient begins inhaling, $\partial CO_2$ becomes sharply negative and image acquisition terminates. Images are obtained for 30–90 seconds. Reduction of organ motion is documented radiographically and corresponds to the motion that will be obtained when the same gating algorithm is used to gate a linear accelerator. Table 3 sets forth the values for the measured parameters which may be used in effecting the TRIGGER ON and the TRIGGER OFF signals where the CEHFE algorithm is used. The graph of FIG. 5 indicates by the shaded regions at the bottom of the graph when beam on conditions ("G") are met for air flow ("F"), $CO_2$ ("C") and lung volume ("V") using the CEHFE algorithm for a 14 year old female with Hodgkin's disease. Air pressure was not used for this patient and is latched to be always on. When all four parameters indicate beam on a gating signal (G) is sent. Values are normalized for ease of viewing.

TABLE 3

CEHFE Algorithm

| Respiratory Parameter | Trigger On Signal | Trigger Off Signal |
|---|---|---|
| Air Flow | Flow < fraction of immediately previous peak value. User selectable, typical value = 10% | Flow > fraction of immediately previous peak value. User selectable, typical value = 10% |
| Air Pressure | Pressure < fraction of immediately previous peak value. User selectable, typical value = 10% | Pressure > fraction of immediately previous peak value. User selectable, typical value = 10% |
| Lung Volume | Last Max Vol − Current vol > Threshold, $\partial$Vol near 0. Threshold value set graphically, typically avg. diff between adjacent max and min lung volumes. | Last Max Vol − Current vol < Threshold. Threshold value set graphically, typically avg. diff between adjacent max and min lung volumes. |
| $CO_2$ | $CO_2$ > Threshold. User graphically selectable, typical value = 90% of maximum value. | Falls below threshold. |
| $\partial CO_2$ | Not Used | $\partial CO_2$ has large negative value and $CO_2$ < Threshold. |
| Time | N/A | N/A |

Reduction of diaphragmatic movement is dependent on the diaphragm naturally stopping at the same position at the end of each respiratory cycle. Because this occurs quite naturally at the end of exhalation, diaphragm position remains fairly constant during not only any given breath hold, but 1rom one breath hold to the next, In contrast, at the end of inhalation, there is naturally more variability of diaphragm position. Although the diaphragm position will remain fairly constant during any given breath hold, there will be significant variability from one breath hold to the next. Consequently there is greater diaphragm movement using the CEHFI (constant exposure, hold at full inhalation) algorithm than the CEHFE algorithm.

Using biofeedback, a visual or audible cue 37 is transmitted to the patient to hold his or her breath at the instance when all the monitored respiratory parameters fall within an acceptable range and gating commences. Use of red (hold breath) and green lights is one example of visual cues. Use of a computer synthesized voice to instruct a patient when to hold his breath is an example of an audible cue. Beam on occurs only if monitoring of the respiratory parameters indicate that the patient held his breath at the appropriate time. As without biofeedback, beam on continues as long as breath hold continues, mainitaining respiratory parameters within example limits. Use of biofeedback with the CFEHI algorithm reduces diaphragm movement to a range commensurate with the CFEHI algorithm. Biofeedback may also be used to control the time between breath holds. It may be set to initiate breath hold as soon as the next occurrence of all respiratory parameters talling within acceptable limits (i.e, the next respiratory cycle) or after the occurrence. Experience has shown that for the CFEHI algorithm, a lapse of approximately 10 seconds between full inhalation breath holds is optimal Shorter duration leads to patient fatigue, reducing diaphragm reproducibility. Longer duration unnecessarily increases treatment time.

Due to age or medical status, a limited number of patients are unable to hold their breath, In these cases a "continuous exposure, centered about full exhalation" (CECAFE) algorithm is used. Image acquisition begins earlier in the respiratory cycle than for the CEHFE algorithm by setting the threshold for acceptable lung volume higher and acceptable $CO_2$ level lower. Image acquisition is allowed to continue beyond the point that $\partial CO_2$ turns sharply negative (start of inhalation) for a fixed period of time, usually 0.25–0.50 seconds. There is a trade off between the length of image acquisition time and amount of diaphragm motion, with longer acquisition times resulting in greater movement.

Gating treatments on a linear accelerator are carried out using either continuous exposure algorithm (CEHFE or CECAFE), with the hold breath method resulting in less diaphragm motion and requiring a smaller PTV. Prior to treatment each day, a set of training data is obtained with the patient breathing normally, allowing adjustment of the parameter levels used in the gating algorithm. Table 4 sets forth typical parameter conditions for actuating the TRIGGER ON and TRIGGER OFF signals for the CECAFE algorithm.

TABLE 4

CECAFE Algorithm

| Respiratory Parameter | Trigger On Signal | Trigger Off Signal |
|---|---|---|
| Air Flow | Same as CEHFE, but with larger threshold value to trigger earlier in respiratory cycle. | Same as CEHFE, but with larger threshold value to trigger earlier in respiratory cycle. |
| Air Pressure | Same as CEHFE, but with larger threshold value to trigger earlier in respiratory cycle. | Same as CEHFE, but with larger threshold value to trigger earlier in respiratory cycle. |
| Lung Volume | Same as CEHFE, but with larger threshold value to trigger earlier in respiratory cycle. | Same as CEHFE, but with larger threshold value to trigger earlier in respiratory cycle. |
| $CO_2$ | Same as CEHFE, but with larger threshold value to trigger earlier in respiratory cycle. | Falls below threshold. |
| $\partial CO_2$ | Not Used | $\partial CO_2$ has large negative value and $CO_2$ < Threshold. |
| Time | N/A | User selectable period of time after $\partial CO_2$ has large negative value, typically 0.25–0.50 sec. |

A linear accelerator is made to turn rapidly on and off in response to the bating signal. A representative system can provide an industry standard digital signal (5 volt TTL), 5 volt analog signal or change in resistance (i.e, closing a switch via relay) as a gating signal, allowing triggering of a wide variety of linear accelerators. Kubo describes a method for rapidly turning a Varian (Palo Alto, Calif.) linear accelerator in response to a gating signal. (H. Kubo et al., "Respiration Gated Radiotherapy Treatment: A Technical Study", Phys Med Biol, 41:83–91; 1996) Ohara describes an approach for a Mitsubishi accelerator (Osaka, Japan). Port films are obtained using the SEFE algorithm. Longer exposures, as may be required with electronic portal imaging, are accomplished using one of the continuous exposure algorithms (CEHFE or CECAFE). (K. Ohara et al., "Irradiation Synchronized with Respiration Gate", Int J. Radiat Oncol Biol Phys, 17:853–7; 1989).

Shallow breathing marginally reduces diaplhragmatic motion. It is important to remember that the position of the diaphragm at maximum exhalation often remains unchanged from the position during normal respiration. Gating at the mid point of the respiratory cycle, as it has been suggested is at a very non reproducible position and is not recommended. It is important that the position of the diaphragm also be at the point of maximum exhalation in the diagnostic images used for treatment planning. For simulators, this is easily accomplished by a simple modification of the foot pedal circuit used for fluoroscopy and radiograph exposure.

Use of the CEHFE algorithm is applicable to most patients and eliminates much of the diaphragmatic motion, The inventors' experience indicate that most patients receiving thoracic or abdominal irradiation are able to hold their breath for short periods of time. A period of 2–3 seconds seems to be typical. In pediatric patients, the diaphragm moves between 10 and 25 mm. The motion in adults is greater (10–70 mm). The present invention eliminates 80–90% percent of this motion with a doubling or tripling of the treatment time compared to ungated linear accelerator treatments, The use of $CO_2$ levels and its derivative is very important in determining the correct moment to gate the radiation beam. Used in concert with air flow, air pressure and lung volume parameters, this results in an extremely robust method of gating. Appropriate setting of the algorithm parameters results in elimination of almost all false positives (i.e, turning on the beam at an improper point in the respiratory cycle) with the occurrence of only a few false negatives.

The present invention is applicable to a number of areas of medicine in which respiratory induced organ motion is of concern. Depending on the application, the appropriate gating algorithm is selected and the instant system sends either an industry standard digital signal (5 volt TTL), 5 volt analog signal, or change in resistance (i.e. closing a switch via relay) to trigger the medical device.

In radiology, use of one of the single exposure algorithms (SAFE or SEFI) may be used to obtain short exposure x-rays without requiring patients to hold their breath. The continuous exposure algorithms may be used in fluoroscopy or cineradiography. CT, MRI, ultrasound, PET or SPECT gated studies may be obtained by using one of the continuous exposure algorithms (CEHFE or CACAFE) to send a triggering signal to commence or suspend image acquisition. Ritchie and Mori describe a similar method for triggering a commercial CT scanner by modification of the switch that turns x-rays on and off. (C. J. Ritchie et al., "Predictive Respiratory Gating: A New Method to Reduce Motion Artifacts on CT Scans", Radiology 190:847–52; 1994 and M, Mori et al., "Accurate Contiguous Sections Without Breath-Holding on Chest CT: Value of Respiratory Gating and Ultratfast CT", AJR Am J Roentgenol, 162:1057–62, 1994). The present invention results in greater accuracy than those methods already in use that make use of analysis of single respiratory parameters using impedance plethysmography. Because the present invention employs a sensor placed in the patient's mouth, there is no risk of image artifacts caused by a mechanical device placed on the abdomen or thorax that intersects the imaging plane. In MRI, use of navigator echo techniques appears to be a promising approach to minimize respiratory motion. The present invention, used in conjunction with navigator echo techniques may further minimize motion or help freeze motion at a particular point in the respiratory cycle. In MRI systems in which navigator echo techniques are not available, the invention may serve as an adequate substitute.

Lithotripsy and laser surgery operate in a burst mode in which ultrasonic or light waves are directed at the patient at fixed points in time. Use of the present invention to trigger at a particular point in the respiratory cycle makes targeting of the kidneys easier in lithotripsy and targeting of abdominal and thoracic organs simpler in laser surgery.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

What is claimed is:

1. A method for gating therapeutic or diagnostic energy to a tissue volume of a medical patient during a selected portion of the patient's respiratory cycle, to thereby diminish inaccuracies in the assumed spatial position of the tissue volume arising from displacements induced by the patient's respiration; said method comprising:
    monitoring the gases flowing to and from the patient's lungs to provide quasi-continuous measurements as a function of time, of at least two of (a) flow rate, (b) pressure, (c) patient lung volume and (d) carbon dioxide concentration;
    utilizing the said measurements to trigger the time period during which the said energy is gated on, at the beginning of the selected portion of the respiration cycle; and
    terminating the time period during which the said energy is gated on, at the end of the selected portion of the respiration cycle.

2. A method in accordance with claim 1, wherein said selected portion of the respiration cycle starts at substantially full exhalation.

3. A method in accordance with claim 2, wherein the selected portion of the respiration cycle includes a respiration hold introduced in the cycle by the patient at said substantially full exhalation.

4. A method in accordance with claim 3, wherein said energy is gated on when at the same time (1) said gas flow rate and pressure are below predetermined levels; (2) said lung volume is below a predetermined threshold level; and (3) the carbon dioxide level is above a preselected level.

5. A method in accordance with claim 4, wherein said predetermined levels for said flow and pressure are less than a user selectable fraction of the immediately previous peak values for said parameters; and wherein said preselected carbon dioxide level is a selected fraction of its maximum value.

6. A method in accordance with claim 4, wherein said energy gating period is terminated independently of one or more of measurements (a) through (d).

7. A method in accordance with claim 4 wherein said energy gating period is terminated when (1) said as flow and pressure are greater than a predetermined fraction of the immediately previous peak values of said parameters; and (2) the difference between the last maximum value and the current value of said lung volume is greater than said predetermined threshold value, OR the time rate of change of said lung volume has changed from being substantially zero; and (3) the concentration of said carbon dioxide falls below a selected threshold value, and (4) the time rate of change of said carbon dioxide concentration has a substantially negative value.

8. A method in accordance with claim 7, subject to the further condition for energy gating termination that (5) a preselected time period has transpired following occurrence of condition (4).

9. A method in accordance with claim 1, wherein said selected portion of the respiration cycle is initiated at substantially full inhalation.

10. A method in accordance with claim 9, wherein a hold is introduced in the respiration cycle by the patient at said substantially full inhalation.

11. A method in accordance with claim 10, wherein said energy is gated on when at the same time (1) said gas flow rate and pressure are below predetermined levels; (2) said lung volume is above a predetermined level and the time rate of change of the lung volume is substantially zero; and (3) the carbon dioxide level is below a preselected level.

12. A method in accordance with claim 11, wherein said predetermined levels for said gas flow and pressure are less than a selected fraction of the immediately previous peak values for said parameters; and wherein said carbon dioxide level is substantially zero.

13. A method in accordance with claim 1, wherein said selected portion of the respiratory cycle is centered about full exhalation.

14. A method in accordance with claim 1, wherein the said energy is electromagnetic.

15. A method in accordance with claim 14, wherein the said energy comprises x-rays.

16. A method in accordance with claim 14 wherein the said energy is at visible or near visible frequencies.

17. A method in accordance with claim 14, wherein the said energy comprises an activating field for MRI diagnosis.

18. A method in accordance with claim 1, wherein the said energy is in the form of a particle beam.

19. A method in accordance with claim 1, wherein the said energy is sonic.

20. A method in accordance with claim 1 wherein the said measurements are utilized to control a gating signal which activates a source of the energy.

21. A method in accordance with claim 1, further including generating a visual or audible cue to the patient to signal the patient to hold his or her breath when all monitored respiratory parameters fall within a selected range.

22. A method in accordance with claim 21 wherein the selected range is that which commences gating.

23. A method in accordance with claim 21, wherein gating is commences and continues only while the breath is held, as determined by the measured respiratory parameters.

24. A system for gating of energy to a tissue volume of a medical patient during a selected portion of the patient's respiratory cycle, to thereby diminish inaccuracies in the assumed spatial position of the tissue volume arising from displacements induced by the patient's respiration; said system comprising:

a controllable source of radiated energy for gating said energy to said patient tissue volume in response to an ON/OFF control signal;

means for monitoring the gases flowing to and from the patient's lungs and providing quasi-continuous measurements as a function of time for any selected subset of (a) flow rate, (b) pressure, (c) patient lung volume and (d) carbon dioxide concentration;

means for utilizing said measurements to trigger said source control signal to ON at the beginning of the selected portion of the respiration cycle; and means for triggering said control signal to OFF at the end of the selected portion of the respiration cycle.

25. A system in accordance with claim 24, wherein said source generates electromagnetic energy.

26. A system in accordance with claim 24, wherein said source generates sonic energy.

27. A system in accordance with claim 24, wherein said source generates a stream of energetic particles.

28. A system in accordance with claim 24, wherein said means for triggering said control signal to OFF effects said triggering in response to said measurements.

29. A system in accordance with claim 28, wherein said means for triggering said control signal to OFF effects said triggering independent of said measurements.

30. A system in accordance with claim 28, wherein said means for triggering said control signal to OFF effects said triggering as a function of elapsed time from the triggering of said control signal to ON.

31. A system in accordance with claim 24, wherein the selected portion of the patient's respiratory cycle starts at full inhalation.

32. A system in accordance with claim 24, wherein the selected portion of the patient's respiratory cycle starts at full exhalation.

33. A system in accordance with claim 24, wherein the selected portion of the patient's respiratory cycle is centered about full exhalation.

34. A system in accordance with claim 24, further including means for generating a visual or audible cue to the patient to signal the patient to hold his or her breath when all monitored respiratory parameters fall within a selected ranges.

35. A system in accordance with claim 34 wherein the selected range is that which commences gating.

36. A system in accordance with claim 35, wherein gating is commences and continues only while the breath is held, as determined by the measured respiratory parameters.

* * * * *